US 6,537,801 B1

(12) United States Patent
Ida et al.

(10) Patent No.: US 6,537,801 B1
(45) Date of Patent: Mar. 25, 2003

(54) BIOCHIP AND BIOCHIP READING DEVICE COMPRISING A PLURALITY OF ZONES FOR MOLECULAR RECOGNITION

(75) Inventors: Michel Ida, Voreppe (FR); Alain Fargeix, Meylan (FR); François Perraut, Saint Joseph de Rivière (FR); Alexandre Lagrange, St. Egreve (FR)

(73) Assignees: Commissariat a l'Energie Atomique, Paris (FR); Biomerieux S.A., Marcy l'Etoile (FR)

( * ) Notice: Subject to any disclaimer, the term of this patent is extended or adjusted under 35 U.S.C. 154(b) by 0 days.

(21) Appl. No.: 09/787,894
(22) PCT Filed: Oct. 4, 1999
(86) PCT No.: PCT/FR99/02359
§ 371 (c)(1),
(2), (4) Date: Mar. 28, 2001
(87) PCT Pub. No.: WO00/20861
PCT Pub. Date: Apr. 13, 2000

(30) Foreign Application Priority Data

Oct. 5, 1998 (FR) .............................. 98 12438
Jul. 23, 1999 (FR) .............................. 99 09588

(51) Int. Cl.$^7$ ............... C12Q 1/68; C12P 19/34; C07H 21/02; C07H 21/04; C07H 19/00
(52) U.S. Cl. ............... 435/287.2; 435/6; 435/7.1; 435/91.1; 435/91.2; 435/287.2; 536/22.1; 536/23.1; 536/24.3; 536/24.31; 536/24.32; 536/24.33; 356/394
(58) Field of Search ............... 435/6, 7.1, 91.1, 435/91.2, 287.2; 536/22.1, 23.1, 24.3–24.33

(56) References Cited

U.S. PATENT DOCUMENTS

| 4,299,494 A | 11/1981 | Badoz et al. |
| 5,646,411 A | 7/1997 | Kain et al. |
| 5,721,435 A | 2/1998 | Troll |
| 5,790,710 A | 8/1998 | Price et al. |

FOREIGN PATENT DOCUMENTS

| EP | 0 640 826 | 3/1995 |
| WO | WO 98/01533 | of 1998 |
| WO | WO 98/28623 | 7/1998 |
| WO | WO 98/38490 | 9/1998 |

OTHER PUBLICATIONS

Michel Bellis, et al., Medecine Sciences, vol. 13, No. 11, pp. 1317–1324, "La Puce ADN: Un Multiréacteur De Paillasse", 1997.
Andrew Marshall, et al. Nature Biotechnology, vol. 16, pp. 27–31, "DNA Chips: An Array of Possibilities", Jan. 1998.
S.E. Bialkowski, vol. 137, 6 pages. "Photothermal Spectroscopy Methods for Chemical Analysis", (Table of Contents only).
A.C. Boccara, et al., Appl. Phys. Lett., vol. 36, No. 2, pp. 130–132, "Thermo–Optical Spectroscopy: Detection by the "Mirage Effect"", Jan. 15, 1980.
Fotios K. Fotiou, et al., Applied Spectroscopy, vol. 40, No. 5, pp. 704–706, "Hadamard Transform Photothermal Deflection Imaging", 1986.
Andrei D. Mirzabekov, Tibtech, Elsevier Science, vol. 12, pp. 27–32, "DNA Sequencing by Hybridization—A Megasequencing Method and a Diagnostic Tool?", Jan. 1994.

*Primary Examiner*—Jeffrey Siew
(74) *Attorney, Agent, or Firm*—Oblon, Spivak, McClelland, Maier & Neustadt, P.C.

(57) ABSTRACT

A device for reading a biochip including plural molecular recognition areas and plural optical positioning marks, associated with recognition areas. The device includes an optical head capable of projecting excitation light onto the biochip. A device is provided to effectuate relative displacement between the head and the biochip. A first optical analysis system is associated with the optical head to receive any light arriving from recognition areas. A second optical positioning system is associated with the optical head to receive any light from at least one guide track and/or optical positioning mark. A device is further provided for servo-controlling scanning by the optical head. Such a device may find particular application to biological and chemical analysis.

31 Claims, 6 Drawing Sheets

BIOCHIP AND BIOCHIP READING DEVICE COMPRISING A PLURALITY OF ZONES FOR MOLECULAR RECOGNITION

DESCRIPTION

1. Technical Field

This invention relates to a biochip comprising several molecular recognition areas and a device for reading such a biochip. A biochip means any chip or support with one or several areas (called recognition areas) on its surface, equipped with molecules with recognition properties. Throughout the rest of this text, the term biochip is used improperly, independently of whether the chip is used for a chemical or a biological analysis.

For example, recognition molecules may be trace nucleotides, polynucleotides, proteins such as anti-bodies or peptides, lectines or any other ligand-receptor type system. In particular, recognition molecules may include fragments of DNA or RNA.

When the biochip is brought into contact with a sample to be analysed, recognition molecules can interact, for example by complexing or by hybridisation with "target molecules" of the sample. Thus, by equipping a biochip with several recognition areas with different recognition molecules selectively sensitive to different target molecules, it is possible to detect and possibly quantify a large variety of molecules contained in the sample. Each recognition area contains only one type of identical molecules.

Complexes formed on the biochip may be identified by means of fluorescent marking applied to target molecules of the sample.

The read device according to the invention is intended to facilitate the operation to read marked or unmarked molecules that may be present in chip recognition areas.

Recognition areas may be read without the presence of any marker, and this type of technology is already known in the state of the art. In particular, some direct methods of detecting hybridisation include detection of a variation of the mass, a variation of the thickness, and a variation of the index. Photothermal methods are also known, and are described in document 1 that is mentioned in the references at the end of this description. Finally, Boccara et al. have described a photothermal deflection technique in documents 2 and 3. Improvements to this technique were then described in document 4. The references of these documents are given at the end of the description.

Thus, the invention is used for applications in the biological and chemical analysis fields.

Particular applications in the biological analysis field may include the search for polymorphisms and mutations, sequencing by hybridisation and monitoring the expression of genes.

2. State of Prior Art

The number of recognition areas in a chip varies depending on the type of analysis to be carried out. Thus, a distinction is made between "low-density" chips that comprise a few tens to a few hundreds of recognition areas, and "high-density" chips that may comprise several thousand or several hundred thousand areas of this type.

The size of recognition areas on high-density chips is small. The dimensions of these areas are less than 100 $\mu$m, or possibly even less than 10 $\mu$m.

As mentioned above, complexes formed on biochips are marked using fluorescent markers. For example, markers such as fluoresceine or phycoerythrine may be coupled directly on target molecules of the sample to be analysed. Target molecules may also be marked by means of indirect recognition groups such as biotin or digoxigenin.

Thus, when recognition molecules for a given recognition area have interacted or hybridised with marked target molecules, the fluorescent marker is fixed on these areas.

Reading a biochip includes excitation of fluorescent markers under the effect of light called the excitation light directed at the chip, and then recording of the fluorescence caused by the excitation light for each recognition area.

Detection of fluorescence in a recognition area enables a decision about the presence of target molecules (marked molecules) that could interact with the known recognition molecule, in the sample to be analysed, knowing the type of recognition molecule present in this area. The intensity of the fluorescence may possibly be measured to deduce the concentration of the target molecules concerned in the sample.

The reader can refer to documents such as 6, 7 and 8 for examples of these techniques, particularly for genetic biology applications. The references of these documents are given at the end of this description.

For low-density biochips, recognition areas may be read with imagery stations equipped with charge coupled devices (CCD). These stations are not very well adapted to high-density chips. CCD cameras should have a larger number of detection pixels, and since fluorescence light fluxes are particularly low for high-density chips, the cameras also need to be cooled to improve their signal to noise ratio.

Thus, for high-density chips, fluorescence scanners are used to scan the chip so that the recognition areas can be analysed in sequence.

These scanners are provided with a confocal optical system associated with a photo-electric sensor, to record the fluorescence in each area. The scanner can be used to observe objects with a very good spatial resolution (from 1 to 10 $\mu$m) and the confocal optical system is a means of overcoming parasite light emission effects (auto-fluorescence, specular reflection, etc.).

As an illustration of a scanner for high-density chips, the reader could refer to document 4, the reference of which is also given at the end of the description.

Fluorescence scanners output electrical signals that are acquired to form a two-dimensional image of the biochip. The signals are also used to recognise the spatial structure of the surface of the biochip and to identify and delimit the recognition areas located on it.

Finally, the intensity of the signal for each recognition area is recorded as the result of the analysis.

These analysis results can then be subjected to an appropriate computer processing to obtain biologically or chemically relevant information.

It is found that the signal processing mentioned above has the disadvantage that a larger number of measurement points, or pixels, are required for each recognition area.

A precise delimitation of each recognition area requires a sufficiently high pixel-image density for each recognition area.

In practice, it is found that the number of pixels needs to be of the order of 36 to 64 for each recognition area, depending on its size, to be able to perform signal processing under acceptable conditions.

Thus, signal processing for high-density biochips requires major computer data processing and storage means. Therefore, processing is expensive.

Furthermore, segmentation of the image based on recognition areas is not perfectly reliable.

Documents 9 and 10 mentioned in the references at the end of this description describe other possible means of reading a biochip that avoid some of the difficulties mentioned above.

Document 9 describes how to place recognition and marking elements on the chip to make reading easier, making it possible to envisage reading biochips using reading devices such as compact optical disk players (CD-ROM).

In document 9, the authors describe a chemical treatment for biochips to make them readable on a reading device distributed to the general public (and particularly CD-ROM compact optical disk players). Before analysing the sample containing target molecules to be analysed, molecular recognition areas on the biochip are covered with a reflecting film formed by metallic balls anchored to its surface by "bridge" molecules. These reflecting balls are functionalised to make them bond to target molecules in the sample. Therefore during hybridisation, the same target molecule needs to be bonded at two points; firstly to the surface of the biochip on molecular recognition areas, and secondly to the surface of one of the metallic balls located above this recognition area. After hybridisation, an appropriate chemical treatment breaks the bridge molecules anchoring the metallic balls to the surface, and the surface of the biochip is rinsed. Only the metallic balls retained at the surface by a minimum number of target molecules are present at this time, and form biological information "bits".

After the processing proposed in document 9, an additional biochemical step is necessary for the analysis. This step involves the cleavage of bridge molecules. Furthermore, hybridisation of target molecules on recognition areas is very much slowed down by the presence of metallic balls that considerably reduce the rate of diffusion of target molecules towards the surface supporting the recognition areas. Therefore, the analysis can be very slow. Furthermore, the relation existing between the number of metallic balls remaining finally bonded to the surface and the initial concentration of target molecules in the sample, cannot be easily quantified. It is more like a step type relation. (There is a threshold below which the balls are not bonded and above which they are bonded. The dynamic range within which there is an intermediate number of attached balls, and therefore a number that can be quantified, is probably very small).

According to document 10, the biochip is provided with marks associated with recognition areas. However, these marks are distinct from the recognition molecules and are physically separate from recognition areas. The marks may be detected independently of a hybridisation or complexing reaction when the biochip is scanned.

As soon as the position of the marks is known, the time elapsed between successive detection of two marks can be measured, to establish a function determining the relative position of the scanner on the biochip. This function can be used to more precisely determine the location of the recognition areas on the biochip.

The use of marks on the biochip is a permanent means of improving the positioning of measurement areas and thus facilitating reading.

However, the relative displacement between the biochip and/or the scanner optical reading system need to be controlled sufficiently accurately for precise guidance of the optical scanner system on the recognition areas.

This control is not particularly difficult when the recognition areas are sufficiently large and there are not many of them. The relative displacement between the biochip and the optical system may be made efficiently using relative inexpensive mechanical means.

However, for high-density chips for which the dimensions of the recognition areas do not exceed a few microns, extremely precise mechanical means are essential in order to achieve satisfactory scanning of recognition areas and to obtain a sharp and undeformed image.

Extremely precise mechanical means are also necessary to achieve scanning of small recognition areas at a regular speed so that the image obtained can be corrected, and so that the image can be used as a function of the displacement.

As an illustration, consider the example of a high-density chip comprising for example 300×300 adjacent recognition areas with a 20 $\mu$m side, and for a typical 7×7 points measurement sample, a displacement resolution of 3 $\mu$m is necessary, the precision of this displacement must be 1 $\mu$m (±0.5 $\mu$m) and the positioning repeatability must be 1 $\mu$m (±0.5 $\mu$m). The displacement speed must be constant and the scanning displacements must be parallel within 0.3 mrad. Inexpensive mechanics cannot achieve these characteristics.

Furthermore, the chip has to be oriented in space and displaced with a resolution of 10 $\mu$m, a precision of about 5 $\mu$m and a repeatability of the order of 10 $\mu$m, in order to focus the optical system before the chip is read. These characteristics are given for a 100 $\mu$m section depth of the optical system. A reduction in the depth of the section to 10 $\mu$m would then require a minimum resolution of 2.5 $\mu$m, a precision of 0.5 $\mu$m and a repeatability of 1 $\mu$m, on the focussing.

The need for high precision mechanical means is why biochip reading devices are particularly expensive.

Furthermore, since high-density biochip recognition areas have a small surface area, the biochips have to be scanned slowly to be able to collect a sufficient quantity of light energy for each sample of each recognition area.

However, slow scanning makes the analysis of the biochip excessively long whenever there is a large number of recognition areas.

The light quantity produced by fluorescence may be increased slightly by exciting the target molecule markers by means of powerful lasers. However, the use of this type of equipment further increases the cost of read devices.

Documents 11, 12 and 13 also illustrate the state of the art. Document 11 relates to detection and quantification of cells, but not to molecular recognition. Documents 12 and 13 describe read systems using slow positioning mechanisms that do not cause reading problems "in real time".

DESCRIPTION OF THE INVENTION

One purpose of this invention is to propose a biochip read device that does not have the difficulties mentioned above.

One purpose in particular is to propose such a device at low cost capable of reading high-density biochips.

Another purpose is to propose such a device capable of more quickly scanning chips, and thus reducing the analysis time without reducing the measurement quality.

Yet another purpose is to propose a device capable of quickly identifying the position and orientation of a recognition area without making an oversampled acquisition of the chip image.

Another purpose of the invention is to propose a biochip adapted to the said reading device in order to minimize the cost of scanning mechanisms.

In order to achieve these purposes, the objective of the invention is more precisely a device for reading a biochip comprising several recognition areas and several optical positioning marks, in real time, the recognition areas comprising fragments of DNA or RNA and occupying predetermined positions relative to the optical positioning marks, the device comprising:

- an optical head capable of projecting incident light onto the biochip,
- means of relative displacement between the head and the said biochip, capable of scanning over the biochip,
- a first optical system called an analysis system associated with the said optical head to project light possibly coming from recognition areas, onto at least a first electro-optic sensor,
- a second optical system called a positioning system associated with the optical head to project any light from at least one positioning mark, onto at least one second electro-optic sensor, and
- means of servocontrolling the means of displacing the said optical head to control these displacement means as a function of electrical signals from the electro-optic sensor in the optical positioning system, in which:
  - the displacement means comprise macroscopic (large scale) displacement means and microscopic (small scale) displacement means and in which
  - the servocontrol means are connected to the microscopic displacement means.

In the rest of this text, the expression "light from marked molecules . . . " will be used for convenience to refer to light that may be emitted as fluorescent light, or reflected or diffused or refracted from recognition areas in response to incident light, for example by specific groups used on marked or unmarked molecules.

Microscopic displacements are used to refine the position of the optical head along at least one of the three axes. (A first axis corresponding to the optical axis of the first optical system, and two axes perpendicular to the first axis).

A recognition area means a portion of the biochip on the surface of which there are molecules that have the property by which a given type of target molecules can be recognized.

Servocontrolling scanning by the optical head to the positioning system electrical signals is a means of correcting the relative displacement between the chip and the optical head in real time, to obtain extremely precise positioning with inexpensive displacement mechanical means. In particular, it becomes possible to use mechanical means such as actuators that are usually installed on compact disk players.

Servocontrol is also made to achieve a displacement with a relatively uniform velocity to enable continuous reading of the fluorescence of recognition areas.

In this respect, it is worthwhile mentioning that the optical positioning system associated with a servocontrol means provides a means of reading the biochip in real time. In other words, it provides a means of knowing the read position with respect to recognition areas and/or the optical positioning marks, in real time.

Furthermore, the focussing precision obtained by the servocontrol enables the use of a confocal optical system with a shallow section depth so that the influence of parasite light originating from the biochip substrate can be reduced. Thus, better signal dynamics can be obtained.

Optical systems in the read device, unaffected by parasite light due to the low cross-section depth, may be made with a larger digital aperture and consequently collect more light. Consequently, faster reading is possible and/or the incident light source may be less powerful.

According to one aspect of the invention, the relative displacement means may include first macroscopic displacement means (large scale) and microscopic displacement means (small scale). In this case, as mentioned previously, the servocontrol means control the microscopic displacement means.

According to another advantageous aspect of the invention, the optical head may comprise a focussing lens and at least one axial lens focussing displacement actuator. A third optical system called the focussing system may be used with the optical head to project light due to reflection of incident light on the biochip onto a third electro-optic sensor, and focussing servocontrol means may be provided connected to the actuator to control the lens focussing displacement.

Due to the focussing servocontrolling means, recognition areas may be read continuously at the same time as focussing is being done. This characteristic also provides a means of not losing marking on the biochip, such that the measurement precision can be increased independently of scanning conditions.

According to one particular simplified embodiment of the invention, the device may comprise a unique optical system including the first and second optical systems and at least one electro-optic sensor common to the first and second optical systems, the said common optical sensor collecting light not only originating from molecular recognition areas, but also light originating from the positioning marks. The common sensor is then connected to a signal processing system and to means of servocontrolling scanning by the optical head.

Consequently, in this embodiment the common optical sensor outputs signals used for analysis of fluorescence and for servocontrolling the relative displacement between the chip and the optical head (scanning).

The invention also relates to a biochip comprising several recognition areas and several optical positioning marks.

The recognition areas according to the invention are wholly or partly superposed on optical positioning marks so as to cover all or some of the said marks.

For example, the optical positioning marks associated with recognition areas may comprise areas reflecting excitation light. They help to orient the biochip, identify locations of recognition areas, and make a precise scanning independently of whether or not hybridisation was done. In particular, optical positioning marks may be presented in the form of tracks called guide tracks.

According to one particular aspect, the positioning marks may be designed to have a specific reflectivity for incident light, different from the reflectivity of adjacent recognition areas.

According to another particular possible embodiment of the chip, a specific optical mark may be associated with each recognition area. Thus, there is no need to form an image of the entire biochip to determine the location of each area.

Thus, the possibility of precisely determining the location of recognition areas is a means of making precise measurements without oversampling, with a small number of pixels for each recognition area.

Furthermore, as soon as each recognition area is identified, a local analysis can be carried out for one or several given areas by moving the optical head or the chip, in order to aim the head so that it is facing the required area(s) directly.

There are several available possible means of recording light from chip recognition areas.

According to a first possibility, the optical head can be held motionless facing a recognition area and a signal acquisition can be made for a determined time before going onto the next area.

As already mentioned, the optical marks and the servo-control means are used to position the head with sufficient precision so that a reliable analysis can be made. Furthermore, the optical marks are used to precisely position a recognition area even if it does not emit any fluorescent light.

Sensor signals can also be acquired without stopping, by displacing the optical head continuously over several recognition areas placed side by side such that the recognition areas cover the active surface of the biochip, for example by juxtaposition. In this case, the signals are integrated to determine the quantity of light received during the time necessary to scan one or several recognition areas.

However, fluctuations in the displacement speed may affect the analysis of the light quantity emitted per unit time by recognition areas.

Thus, according to a second analysis possibility, it is possible to normalise acquired signals as a function of a time elapsed between when the optical head passes in front of successive positioning marks associated with the scanned recognition areas.

According to a third possibility in which acquisition is also done without stopping, the relative displacement speed between the optical head and the chip can be servocontrolled continuously, by measuring the time elapsed between when the head passes in front of successive marks.

The invention also relates to a biochip that can be read by a device like that described above, in which the molecular recognition areas are superposed on the positioning marks in whole or in part, so as to cover them partially or completely.

This characteristic is particularly advantageous since it prevents congestion of the surface of the biochip by the positioning marks. It means that most or all of the entire surface of the chip can be left available for molecular recognition areas.

Positioning marks are used to orient the biochip, and also to mark and identify recognition areas. This is why they will preferably be located in predetermined positions with respect to the positioning marks.

Very thin positioning marks can be sufficient to position the biochip and/or identify recognition areas.

However, it is found that good precision is only achieved if the surface area of the positioning marks compared with the surface area of the molecular recognition areas with which they are associated, is not negligible.

The characteristic by which positioning marks are arranged so that they are partially or completely overlapped by the molecular recognition areas means that their area can be increased, and thus the servocontrol of position of the biochip relative to the read device can be improved. The read precision is also improved.

When positioning marks are in the form of guide tracks along which an incident light beam will travel for servocontrol of the position, it is desirable that the width of the track is not negligible compared with the width of the light beam.

The track can be marked with excellent precision using positioning marks with a surface that occupies of the order of 30 to 100% of the total area of the chip. overlapping of recognition areas and positioning marks appears even more economically attractive when considering the cost of manufacturing the biochips per unit useful area.

Furthermore, the increase in the area of the positioning marks makes it easier to read the marks and means that read devices can be used with a lower light power and with a lower sensitivity.

This also reduces the cost of the read devices.

The possibility of using a lower intensity light source for positioning reduces the risks of inhibiting or burning fluorescent markers that could be present on molecular recognition areas.

Furthermore, positioning marks may be designed to be almost transparent to at least one fluorescent light that could be emitted from recognition areas in response to at least one incident reading light.

When the laser beam reads through the back face, the reflectivity of the positioning marks and/or an interface between the coating material on recognition areas and the positioning marks may be chosen to be greater than 0%, preferably between 1 and 10%, and more precisely between 1 and 5%.

When the laser beam reads through the front face, the reflectivity of the positioning marks and/or an interface between the coating material on recognition areas and the positioning marks may be chosen to be greater than 0%, specifically between 1 and 100%.

The front and back faces of the biochip refer to the face coated with recognition molecules in the recognition areas (front face) and the opposite uncoated face (back face).

Furthermore, the biochip may comprise an intermediate layer made of a material with a reflectivity different from the reflectivity of the positioning marks, between the positioning marks and the recognition areas. The intermediate layer can then give a determined reflection of incident light on positioning markers, independently of the coating of the molecular recognition areas, and independently of the liquid or gas medium with which the biochip is brought into contact.

Other possibilities can be envisaged for making positioning marks. In particular, they may comprise a sequence of regions with different alternating properties for the incident light.

According to a first possibility, adjacent positioning mark regions may have a different optical path for incident light. The difference in the optical path may be obtained particularly by making adjacent regions from different materials, and/or with different thicknesses, and/or with different doping. The choice of different materials or different doping for adjacent regions means that the refraction indexes for each of them are different.

According to another possible means of making the positioning marks, these marks may be made of strips of bi-refringent material with the property of modifying the polarization direction of an incident polarized read light.

According to yet another possibility, adjacent positioning mark regions may be made from materials with different reflectivities.

Other characteristics and advantages of this invention will become clearer from the following description with reference to the figures in the attached drawings. This description is given purely for illustration and is in no way restrictive.

DETAILED DESCRIPTION OF EMBODIMENTS OF THE INVENTION

Figure 1:
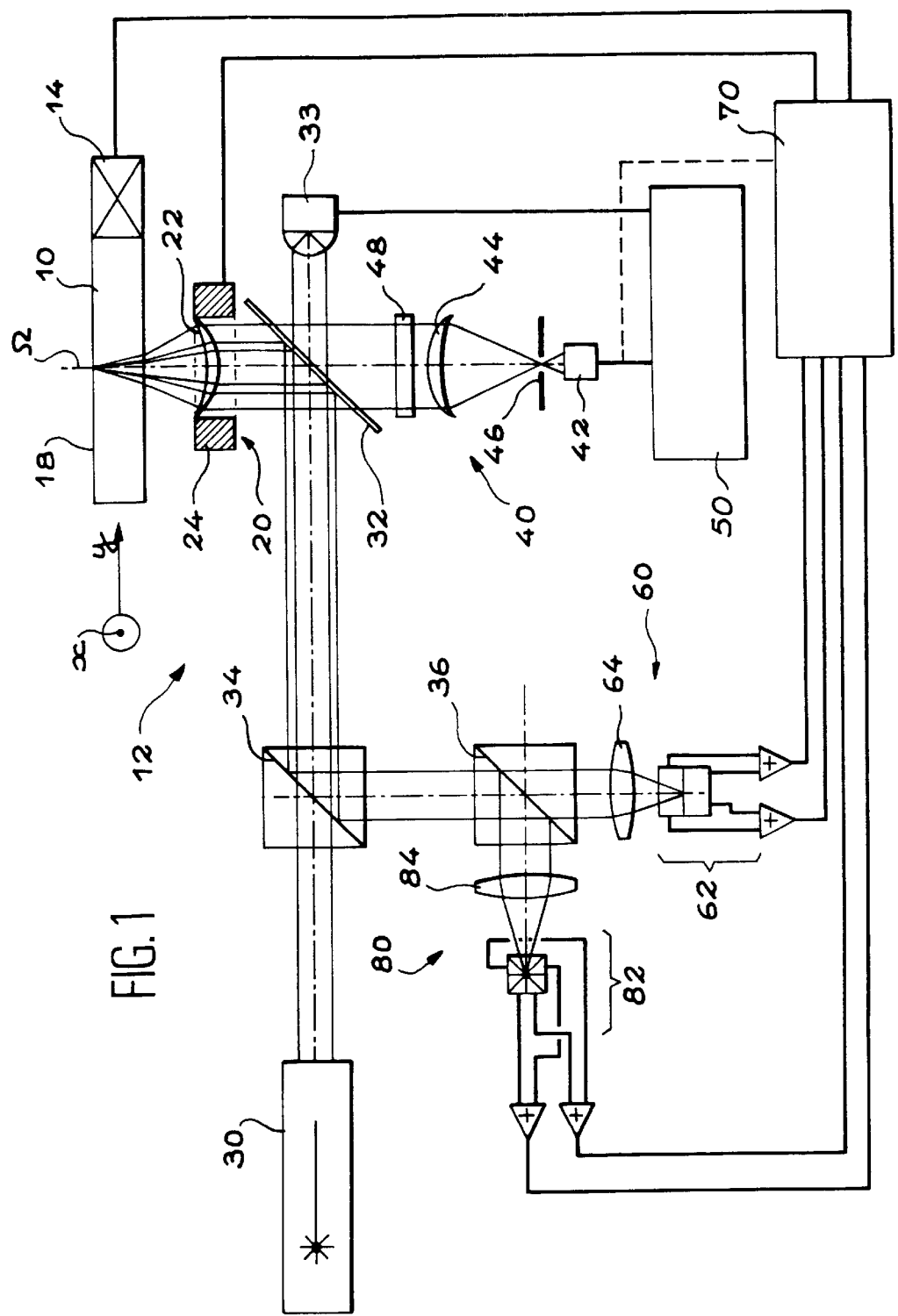
FIG. 1 is a simplified schematic presentation of a read device according to the invention.

Reference 10 in FIG. 1 denotes a biochip with several recognition areas equipped with specific recognition molecules, and possibly guide tracks and/or optical positioning marks associated with the recognition areas. These elements are described in more detail in the rest of the text and are not shown in FIG. 1 for simplification reasons.

In the example described, specific recognition molecules are marked by fluorescent groups, but these groups may be replaced by groups capable of reflecting, diffusing or diffracting light, without going outside the framework of the invention.

The chip is placed facing a read device 12. This device is intended to scan the recognition areas to excite molecules with fluorescent markers fixed on recognition areas, and to record fluorescent light produced by these molecules.

Recognition areas are scanned by relative displacement between the read device or part of the read device 12, and the biochip 10.

In the example shown in FIG. 1, the macroscopic relative displacement is achieved by means of actuators 14, for example motor driven actuators that move the biochip 10. A microscopic displacement of the lens 22 is obtained by means of an electromagnetic actuator 24. The rectangular-shaped biochip is moved in a plane perpendicular to an optical axis Ω of the read device.

This plane is also perpendicular to the plane of the figure.

The displacement may take place along two perpendicular directions x and y shown in the figure.

The read device 12 comprises an optical head 20 with a focussing lens 22 with an optical axis Ω. The optical head lens performs a two-fold function of directing excitation light towards the biochip and collecting fluorescent light emitted in response to the excitation light.

The excitation light is monochromatic light with a first wavelength, for example of the order of 633 nm. It is produced by a laser 30, the beam of which is directed towards the optical head 20 by means of a dichroic mirror 32. The focussing lens 22 is designed to focus the beam on a back face 18 of the biochip, called the active face.

The dichroic mirror 32 reflects most (80 to 95%) of light from the laser to the focussing lens. The remaining part of the light (5 to 20%) passes through the mirror 32 and is collected by an electro-optic sensor 33 called the reference sensor.

The reference sensor 33 measures variations with time of the intensity of the beam emitted by laser 30. This measurement is used for the analysis of fluorescence emitted by the biochip so that the analysis can be made independent of variations in the intensity due to the laser.

A first optical analysis system 40 is associated with the optical head, and is aligned on the optical centreline Ω to project fluorescent light produced by marked excited molecules, possibly present on the biochip on one (or more) electro-optic sensor(s) 42, called analysis sensors in the rest of the text.

More precisely, fluorescent light is collected and collimated by the focussing lens 22 of the optical head 20, to form a beam. This beam passes through the dichroic mirror 32 and then passes through a convergence lens 44 that converges it onto a diaphragm 46. The diaphragm may be formed by making a small hole in an opaque screen. It performs a spatial filtration along the optical centreline Ω and makes the optical system confocal.

The diaphragm, combined with the intermittently illuminated object, only allows light from the area that is illuminated (by the excitation light) to pass in a thin "slice" representing an object plane. The attraction of a confocal system of this type is obvious, particularly for reading DNA chips. The possibility of defining a "slice" of the object space is used to isolate a plane of interest containing molecular recognition areas, from the rest of the chip (glass support, buffers). Therefore, received light does not contain any parasite light from coloured centres on the support, and does not contain a continuous light background.

The fluorescence phenomenon of fluorescent markers carried by the target molecules retained on the recognition areas, converts excitation light into light with a wavelength longer than the wavelength of the excitation light.

For example, in the example described the wavelength of the fluorescent light may be 670 μm.

An interference filter 48 is arranged between the focussing lens 22 of the optical head and the convergence lens 44. It isolates a spectral band corresponding approximately to the fluorescence spectral band in the light received by the optical analysis system. Parasite light is thus better eliminated.

The reference 50 denotes a processing unit for signals output by the analysis sensor 42. In the example described, the analysis sensor 42 is a photo-multiplier sensor that outputs an analog signal proportional to the received fluorescent light intensity.

The signal from the analysis sensor may be integrated for a time period during which the optical head receives light from a given recognition area. As mentioned above, the signal may also be recorded in a measurement process without stopping, while the chip is being scanned. This signal can also be digitised, so that it can be processed using algorithms adapted to the analysis type being carried out.

It is observed that the processing unit 50 also receives a reference signal originating from the reference sensor 33. Taking account of the reference signal is a means of normalizing signals output by the analysis sensor, that are unaffected by fluctuations in the laser intensity, as mentioned above.

The dichroic mirror 32, associated with a separating cube 34, directs light originating from a reflection, or diffraction, or refraction or diffusion of incident light from the laser onto the biochip, towards a second optical system 60. For example, this reflected light may originate from guide tracks and/or positioning marks arranged on the biochip. If the biochip does not include any guide tracks, the biochip may be deposited on a plate on which there are guide tracks.

The second optical system 60, called the positioning system, comprises a lens 64 that focuses received light on at least one electro-optic sensor 62, such as detectors with four quadrants, or multi-quadrants. associated with an astigmatic beam analysis optical system. The electro-optic sensor 62 may also be provided with a CCD module or a differential photo-resistance or any other positioning measurement system.

The electro-optic sensor of the positioning system is connected to a unit 70 called the servocontrol unit. For example, the servocontrol unit may be used to decode sensor signals to detect when the optical head passes in front of a positioning mark, to count positioning marks found and to control the scanning displacement to follow a series of marks corresponding to a series of recognition areas. The servocontrol unit 70 is connected to actuators 14 and/or 24 for this purpose, to control movements of the biochip and/or the lens 22. It can also be used to dynamically keep the optical head in place along a scanning trajectory imposed by marks arranged on the biochip.

For example, actuators may be controlled such that the light intensity received by the sensor in the optical positioning system is included within a given range of values. The operating point corresponds to a state of equilibrium. A position set value is given and the servocontrol system maintains this set value. For example, an attempt will be made to ensure that the distribution of light intensity on the multi-quadrant detector is always the same.

A second separating cube 36, arranged on the second optical system, directs part of the light from this optical system into a third optical system 80, called the focussing system.

The optical focussing system 80 comprises a lens 84 to focus received light on an electro-optic sensor 82, such as a detector with four quadrants, or multi-quadrants, associated with an astigmatic optical beam analysis system, or a CCD module, or a differential photo-resistance or any other position measurement system.

The light directed on the sensor of the optical focussing system originates from reflection of laser light on the biochip. In particular, it originates from positioning mark or vitreous reflection on the active face of the biochip.

The sensor 82 in the optical focussing system 80 is also connected to a servocontrol unit 70. This unit is designed to control an actuator 24 fixed to the lens 22 on the optical head 20. The actuator 24 moves the lens 22 along its axis Ω in order to continuously correct focussing of the optical systems in the biochip, or more precisely on some parts of the biochip.

For example, the servocontrol unit may be designed to provoke displacement of lens 22 of the optical head such that the surface area of a focussing spot on the focussing system sensor is controlled with respect to the surface (shape and/or position) of a reference spot (for example circular).

According to one simplified embodiment, the electro-optic sensor in the first optical system 40, in other words the optical analysis system, may be used to output electrical signals corresponding to light originating from recognition areas, and signals corresponding to light reflected or diffused by the guide tracks and/or positioning marks.

In this case, the sensor is connected not only to the signal processing unit 50, but also (as shown as a discontinuous line in the figure) to the servocontrol unit 70 to control the relative displacement between the chip and the optical head, and possibly for focussing the optical head lens.

In this embodiment, the read device comprises a single optical system that functionally includes the first, second (and possibly the third) optical systems as described above.

Figure 2:
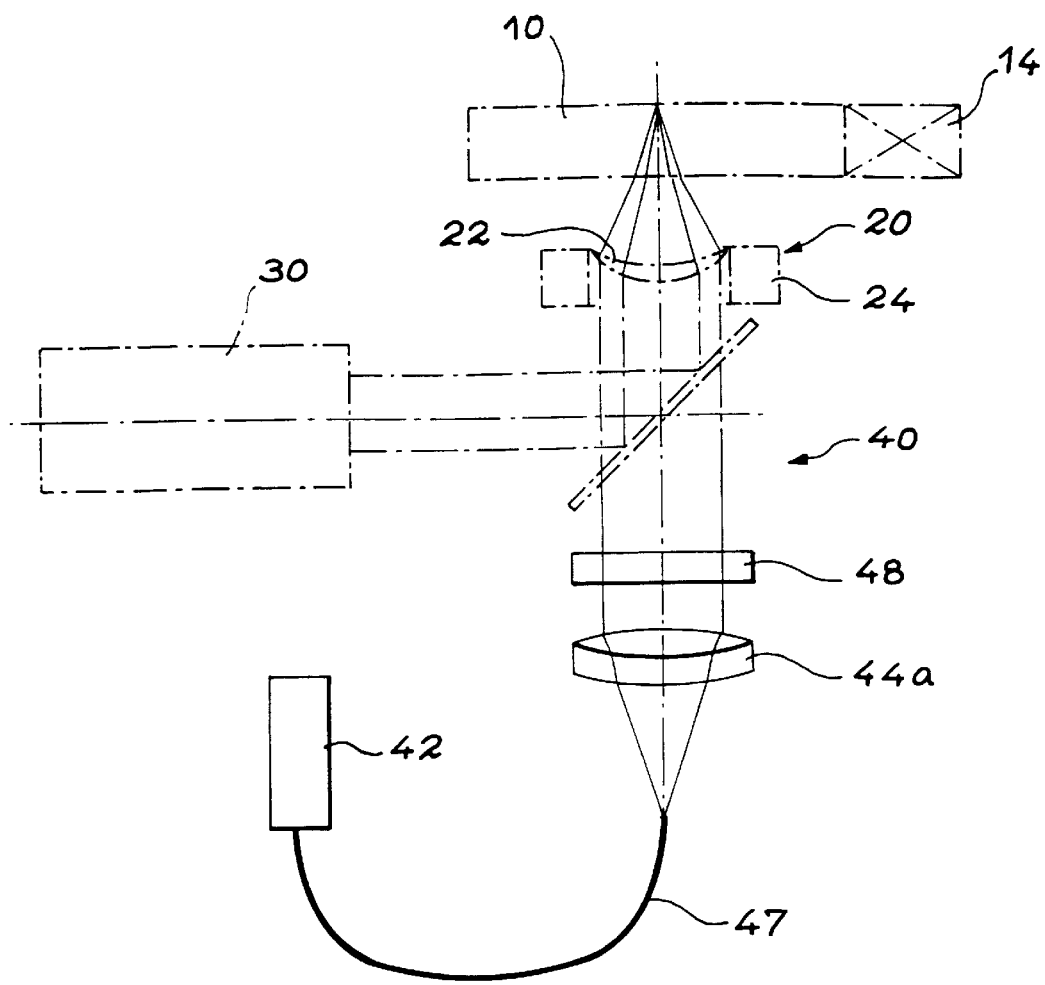
FIG. 2 is a particular schematic presentation of a detail in FIG. 1.

FIG. 2 shows a particular embodiment of the optical analysis system.

For simplification reasons, FIG. 2 only shows a detail of the device, the other elements being identical to those described with reference to FIG. 1.

The optical analysis system 40 in FIG. 2 comprises an interference filter 48 and a focussing objective 44a designed to focus a fluorescent light beam received from the optical head 20 onto a first end of an optical fibre 47.

A second end of the optical fibre 47 is connected to an electro-optic sensor 42, for a photo multiplier or an avalanche photodiode. The optical fibre 47 (slightly multimode) acts as the confocal diaphragm 46 visible in FIG. 1.

The optical analysis systems in FIGS. 1 and 2 are confocal systems, as mentioned above.

The main qualities of a confocal system are its excellent spatial resolution and its excellent axial resolution. The axial resolution represents the capacity of the system to isolate a very small observation volume around the focussing plane, in other words the capacity of eliminating parasite light from outside this volume. It is characterized by a "section depth" of the system denoted Pds.

The section depth Pds, mentioned above, may be expressed by the following formula:

$$Pds = \frac{0.443 \times \lambda}{1 - \cos u}$$

where λ is the wavelength expressed in micrometers and u is the half angle of the digital aperture cone of the optical system.

The lenses used to make the optical analysis system have digital apertures of the order of 0.4 to 0.5. Thus, section depths of the order of 1.8 to 2.8 μm may be obtained. Furthermore, 16 to 22% of the light flux emitted by the biochip is collected by the lens.

We will now describe an example embodiment of a biochip adapted to the read device in more detail.

Figure 3:
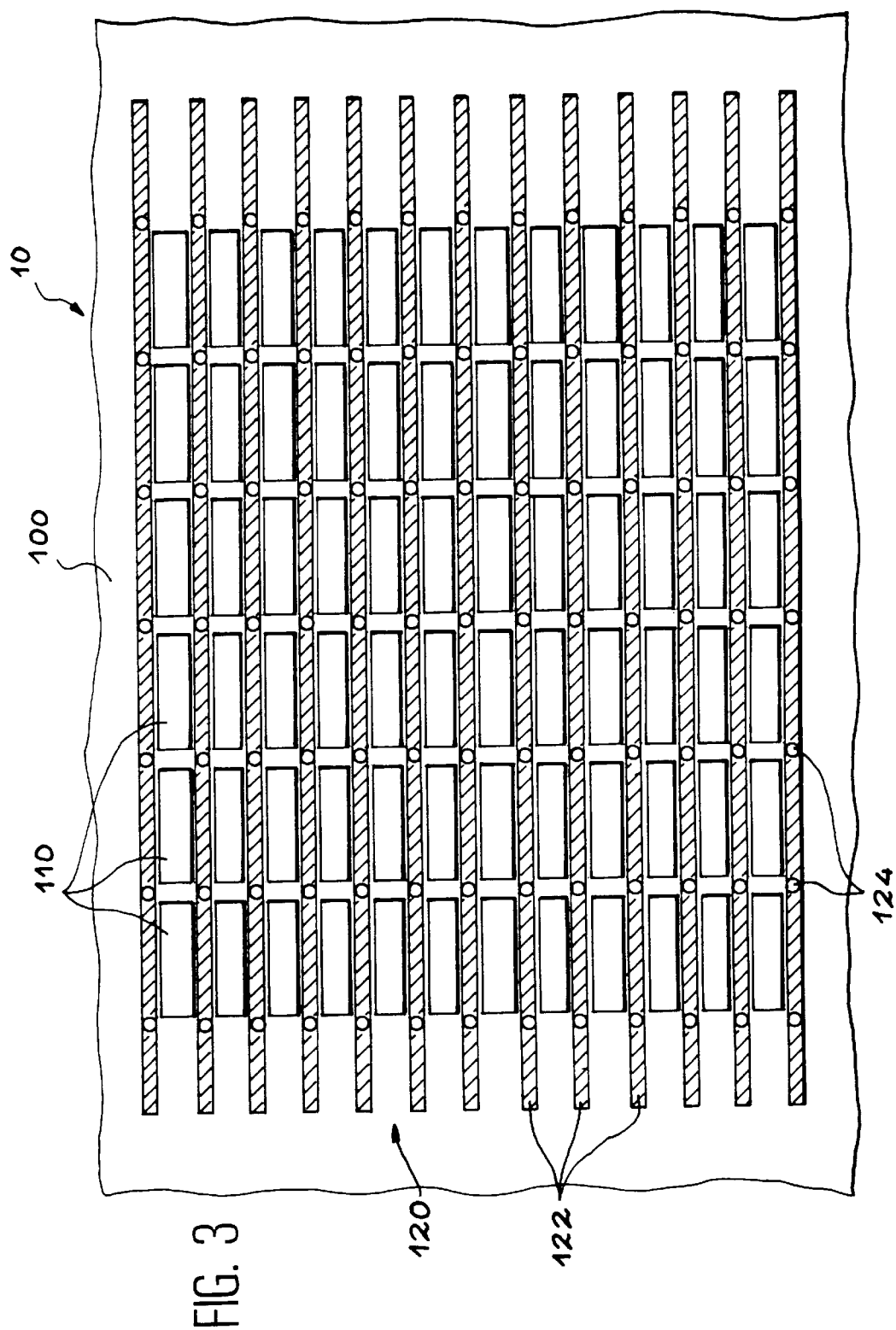
FIG. 3 is a simplified schematic top view of a biochip according to the invention that could be read by the device in FIG. 1.

FIG. 3 shows such a biochip. The biochip 10 comprises a support 100 on which recognition areas 110 are formed. For example, the areas 110 coincide with electrodes formed on the surface of the support. These electrodes were selectively lined with a coating that could interact with a given chemical or biological compound. As mentioned in the introductory part of the text, the coating may in particular comprise recognition molecules capable of hybridising with target molecules.

The various recognition areas 110 are coated with different recognition molecules, specific for the given target molecules.

Each recognition area has a single type of identical molecules. The molecules in a single area are preferably different from the molecules in all other areas.

It is observed that the rectangular-shaped recognition areas 110 are arranged in rows and columns. Other distribution patterns could also be envisaged on the surface of the substrate, for example in circles.

The biochip 10 also comprises a network 120 of optical positioning marks associated with recognition areas. In the example illustrated, this network comprises guide tracks 122 in the form of straight strips extending between the successive rows in the recognition areas.

The guide tracks are reflecting or partially reflecting, fluorescent or diffusing tracks capable of returning part of the excitation light to the device. However, they can also shift the phase, in other words create a difference in the path length during propagation of the return wave. The excitation light returned to the device is analysed by the second and possibly the third optical systems to position and mark the rows of recognition areas and to scan the biochip. The reflecting tracks may also comprise a textured surface with phase shifting etching that can form interference patterns, or introduce a phase shift in the excitation light. These interference or phase shift patterns received by the optical positioning system of the read device may also be used for marking or servocontrolling scanning.

The positioning marks also include optical strips 124 called encoders.

The encoders 124 are preferably located on guide tracks 122 at the beginning and at the end of each recognition area at a pitch corresponding to the size of the said areas.

In one particular embodiment, the encoders may be designed to only slightly reflect light.

For example, encoders are in strips corresponding to an interruption to the reflecting material or an interruption to the textured area of guide tracks 122.

According to another possibility, the tracks may be slightly reflecting and extend along rows of the recognition areas. For example, they may include non-reflecting strips (or encoders).

It is considered that a surface is slightly reflecting when the percentage of light reflected is less than 50%, and preferably less than 5%.

According to one example variant, the chip may also be provided with guide tracks only, that are then reflecting strips.

The association of encoders and more generally optical marks with each recognition area enables particularly fast and precise positioning of areas.

However, it is also possible to associate a single mark with a set of recognition areas, for example one mark for each row or column of recognition areas.

Conventional micro-electronic techniques are used to make marks. For example, they may include the deposition of a metallic reflecting layer such as a layer of aluminium, nickel or chromium as a solid plate, and shaping of this layer by photolithographic etching in accordance with a pattern corresponding to the required positions of the positioning marks.

For example, the metallic layer may be etched using a liquid phase chemical etching process or a gas phase plasma etching process, according to an etching pattern determined by a resin etching mask.

After etching and after removing the resin, a thin layer of silica may be formed on the support in order to improve compatibility of the surface with grafting of biological molecules.

Note that the recognition areas are not necessarily adjacent and that the optical marks are not necessarily located around the periphery of the recognition areas.

According to one possible layout, not shown, optical reflecting marks may be formed inside the recognition areas.

This type of configuration is not a problem when the light from recognition areas is fluorescent light, provided that the distinction between fluorescent light and light reflected by recognition areas is made based on the difference in the wavelength between the two different lights.

If non-fluorescent molecules are detected, but that are diffusing or diffracting (for example), the distinction can be made by frequency encoding of the signals or by making the measurement at an angle different from the angle used for position servocontrols.

After the optical marks have been made, the recognition areas may be coated with recognition molecules. These molecules are synthesized and attached to recognition areas using photolithography synthesis techniques known in themselves.

Note that the surface of the biochip is not perfectly plane. It is of the order of 50 $\mu$m to 200 $\mu$m thicker at the location of the optical mark reflecting strips than elsewhere.

Differences in thickness of this order are small compared with the depth of the section of the proposed optical analysis system.

Operations to make optical marks and to synthesize recognition molecules can be done collectively for a number of biochips on a silicon or glass wafer. This wafer is then cut out to isolate individual biochips manufactured simultaneously.

Figure 4:
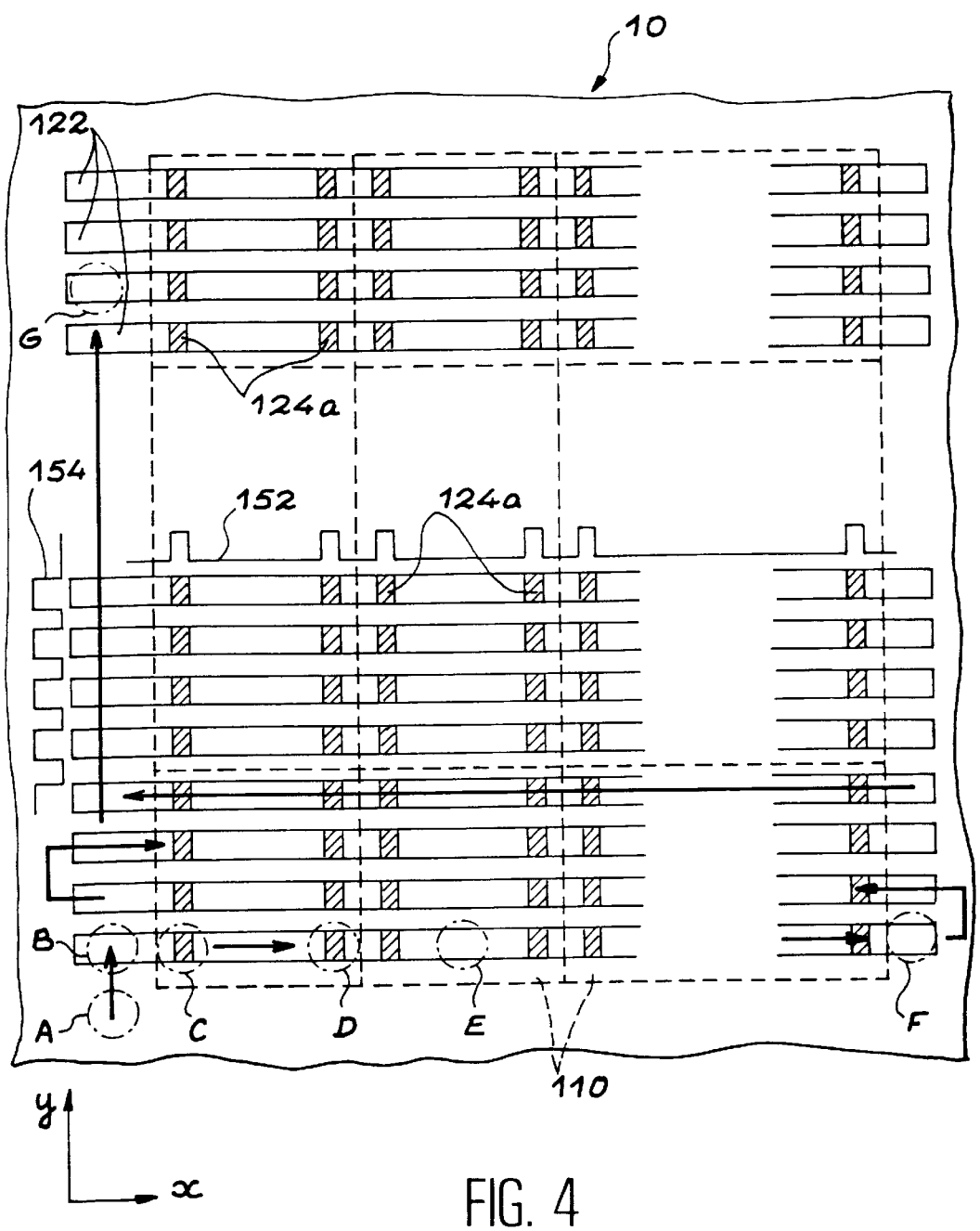
FIG. 4 is a simplified schematic top view of a biochip according to the invention, and illustrates an example read sequence for such a chip.

FIG. 4 also shows a biochip 10 with guide tracks 122 and optical positioning marks in the form of encoders 124 a made of a reflecting material (for example Cr) formed along the tracks 122.

A number of square shaped recognition areas or cells 110 can be seen on the surface of the chip marked by discontinuous lines. Four guide tracks pass through each recognition area.

Schematically, FIG. 4 contains a chain dotted line showing the successive positions of an excitation light spot. The positions are marked by the alphabetic letters A to G.

Chip displacement means (actuator) are such that the movement of the light spot can be broken down into a movement along a first x axis called the fast axis, and along a second y axis called the slow axis.

An example procedure for reading a biochip is shown in table I, which should be read in conjunction with the spot position indicating letters shown in FIG. 4.

Table I indicates the movement made and defines the activation of focussing, positioning and read functions (analysis) for each position.

TABLE I

| | | Function | | |
|---|---|---|---|---|
| Operations | Description | Focussing servocontrol | Positioning Servocontrol | Measurement |
| A | Translation along the slow axis Spot on a corner of the chip Search for focussing | NO => YES | NO | NO |
| B | Translation along the slow axis Search for the beginning of track No. 1 | YES | NO => YES | NO |
| C | Translation along the fast axis Identification of the beginning of cell No. 1 => start the measurement | YES | YES | NO => YES |
| D | Translation along the fast axis Identification of the end of cell No. 1 => end the measurement | YES | YES | YES => NO |
| E | Translation along the fast axis Measure the fluorescence in cell No. 2 | YES | YES | YES |

TABLE I-continued

| | | Function | | |
|---|---|---|---|---|
| Operations | Description | Focussing servocontrol | Positioning Servocontrol | Measurement |
| F | Translation along the slow axis Search for track 2 | YES | NO => YES | NO |
| G | Positioning on a given track Translation along the slow axis Count the number of tracks that pass | YES | NO => YES | NO |

The "track 1" and "track 2" indications show the tracks 122 in order in the y direction starting from the bottom of the figure, and the "cell No. 1", "cell No. 2" indications show successive recognition areas in the x direction starting from left of the figure.

For the reader's information, references 152, 154 in the figures show a signal that could be generated by the sensor in the positioning system when a spot is scanned above the encoders 124a, along the x and y directions respectively.

Figure 5:
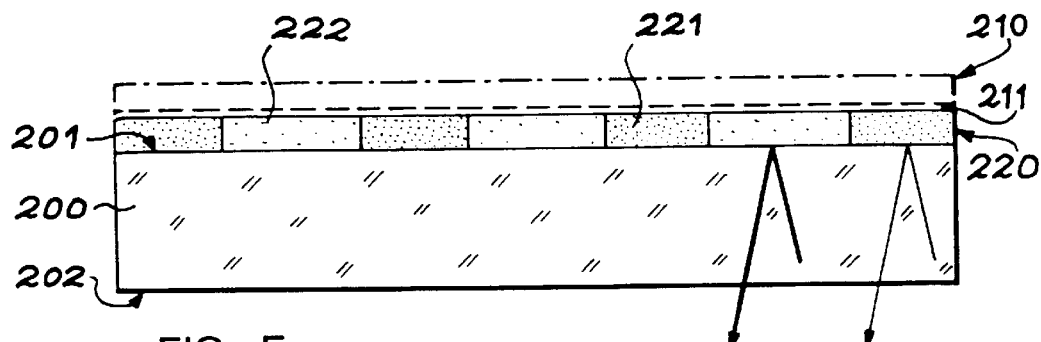
FIGS. 5 to 9 are simplified schematic sections through parts of biochips conform with the invention, illustrating other possible embodiments.

FIG. 5 is a schematic section through part of a biochip on which the references 201 and 202 denote the faces of a substrate 200, called the front and back faces respectively for convenience.

The substrate 200 is made of a material transparent to incident reading light, such as glass. It is covered on its front face 201 by a first layer 220.

The first layer 220 comprises an alternation of adjacent regions 221 and 222, made of a first material and a second material respectively. The first material, for example silicon nitride, has a first reflectivity for incident light, and the second material, for example silicon oxide, has a second reflectivity also for the same incident light that is different from the first reflectivity. The difference between the first and second reflectivity is of the order of 1 to 5%, for example 2%.

Regions 221 and 222 in the first layer may be arranged so as to form a guide track and to form positioning marks.

A second layer 210 is a functional layer that comprises reagents, and forms recognition areas. Further information on this subject is given in the above description.

In this embodiment, as in the other embodiments in FIGS. 6 to 9, the regions 221 and 222 are approximately transparent, in other words incident rays pass through them, and these incident rays are used to read recognition areas. Regions 221 and 222 are superposed with recognition areas and positioning marks that are themselves practically transparent.

The layer 210 may be formed on the first layer directly, or preferably on a bond layer 211 intended to fix the recognition molecules.

The recognition molecules are chosen from among chemical or biological compounds such as DNA probes, antibodies or antigens.

The fact of using a transparent support 200 means that read light can be applied from the back face 202, thus making it easy to put the front face into contact with a medium to be analysed. Rays reflecting on regions 221 and 222 are shown for illustration purposes in the form of arrows.

Figure 6:
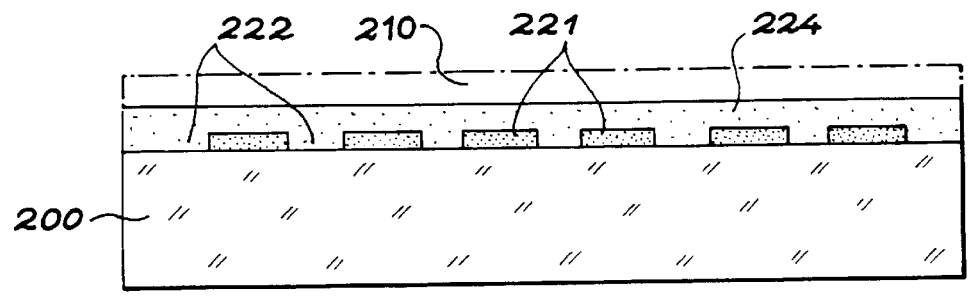

FIG. 6 shows another possible embodiment as a variant to FIG. 5.

A silicon nitride layer is deposited on the support 200 and is etched to define first discontiguous regions 221. A silicon oxide layer 224 is then deposited to coat and cover the first regions 221. The silicon oxide layer thus forms second regions 222 that alternate with the first regions 221 and have a reflectivity different from these regions.

A functional layer 210 covers the silicon oxide layer 224.

Figure 7:
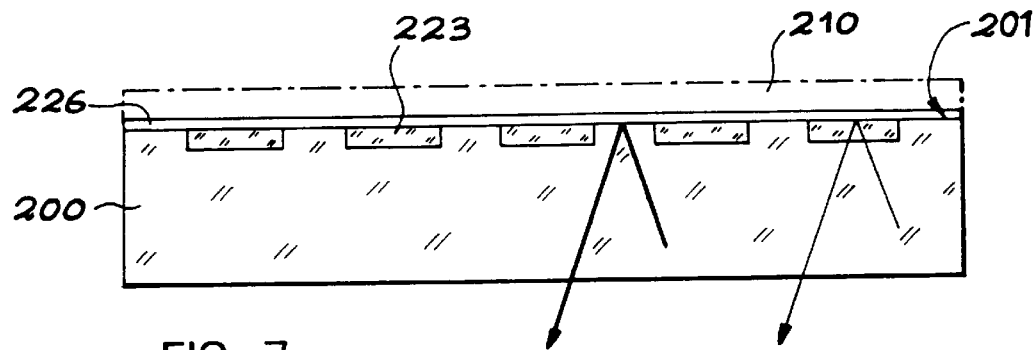

Another possible embodiment of the positioning marks on the biochip is illustrated in FIG. 7.

In this figure, the glass support 200 is doped locally from the front face 201 in order to form discontiguous doped regions 223.

The doped regions 223 thus alternate with intentionally undoped regions of the support, or regions doped with a different concentration.

The difference in doping between regions 223 and the rest of the substrate introduces a difference in index and therefore a difference in the optical path between incident light rays that reach the doped regions and the undoped regions.

The path difference is proportional to the difference between the indexes for doped regions and undoped regions, and introduces a phase shift in the incident rays. This phase shift creates a phase contrast between the different doped and undoped regions. This reading device can detect this phase shift and use it for relative positioning of the chip and marking of recognition areas.

Therefore, the doped regions 223 form positioning marks in the sense according to the invention.

In the example shown in the figure, incident rays are reflected on the upper face of the substrate covered with a functional layer 210.

In order to improve reflection, or at least to guarantee reflection independent of the functional layer and the medium with which it may be put into contact, an intermediate reflection layer 226 (made for example of alumina) may be provided between the support and the functional layer. The index and thickness of this layer are chosen such that the stack of optical thin layers 200, 223, 226 and 210 form a dichroic mirror, the reflectivity of which is controlled according to known optical thin layer deposition techniques. For example, the index for layer 226 will be chosen to be greater than the index for the marks and the support.

The intermediate layer may also act as a bond layer or it may be associated with a bond layer for reagents in molecular recognition areas.

Figure 8:
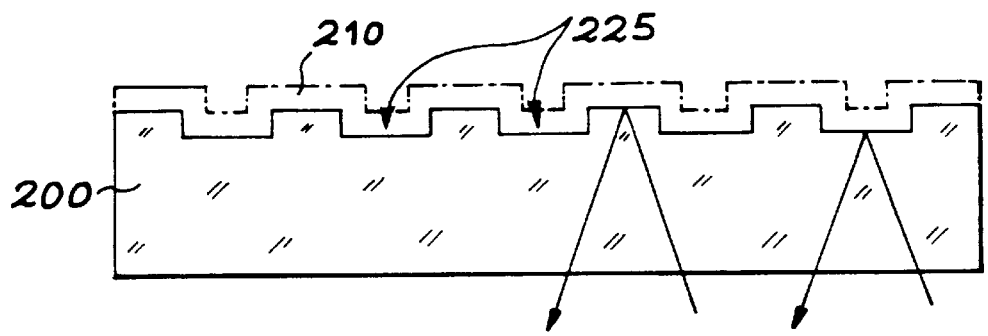

Another possibility for making biochip positioning marks is shown in FIG. 8.

In the example in this figure, positioning marks are obtained by etching discontiguous recesses 225 in the support 200, from its upper face 201. The depth e of the recesses is preferably fixed such that $$e = \frac{\lambda}{4n},$$

where $\lambda$ is the wavelength of incident light and n is the optical index of the support 200.

Light rays reflected on the upper surface in the regions corresponding to the recesses and in unetched regions, pass through different thicknesses of material and thus have a different path length.

The difference in the path length is proportional to the depth of the etching and causes a phase shift between different rays.

In the same way as in the example in FIG. 7, the phase shift creates a phase contrast that can be detected by a read device.

A functional layer 210 forming the recognition areas covers the top face 201.

In the same way as described above, an intermediate layer and/or a bond layer may be provided between the support and the functional layer.

Figure 9:
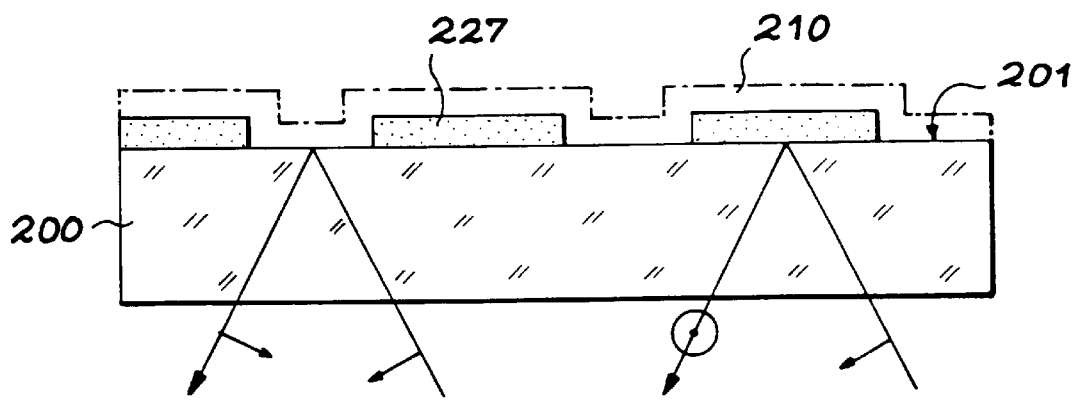

FIG. 9 shows a final example embodiment of the biochip positioning marks.

In this example, the positioning marks are detected by a modification to the polarization of the light that they generate, rather than by a difference in reflectivity or a difference in the optical path.

A layer of bi-refringent material of the rotating or quarter-wave type, is formed on the upper face 201 of the support and is etched to produce positioning marks in the form of disconnected regions 227.

When an incident light ray polarized along a first direction reaches a region 227 of bi-refringent material and passes through it or is reflected on it, its polarization direction is modified by rotation. On the other hand, the polarization of a polarized ray that reaches the bare glass of support 200 is unchanged after reflection.

Positioning marks can thus be detected by inserting a component into the optical positioning system of the read device to select the initial or modified polarization direction. For example, this component may be an analyser.

Advantageously, positioning marks become "invisible" if the analyser is neutralized or removed.

As in the previous examples, the substrate is lined with a functional layer 210. It may also be provided with an intermediate layer as described above.

Documents Mentioned (1) "Photothermal spectroscopy methods for chemical analysis", S. E. Bialkowski, vol. 137 in chemical analysis: a series of monographs on analytical chemistry and its applications, Wiley.
(2) J. Appl. Phys. Lett. 36, 130 (1979).
(3) U.S. Pat. No. 4,299,494
(4) Fotiou and Morris, Appl. Spectrosc. 40, 704 (1986)"
(5) U.S. Pat. No. 5,646,411
(6) "La puce ADN: un multiréacteur de paillasse (The DNA chip: a counter-top multireactor)" by M. Bellis and P. Casellas, in Médecine/Sciences, No. 11, vol. 13, 1997, pages 1317 to 1324
(7) "DNA sequencing by hybridisation—a megasequencing method and diagnostic tool?"—by A. D. Mirzabekov in TIBTECH, volume 12, January 1994, pages 27–32, Elsevier Science
(8) "DNA chips: An array possibilities" by A. Marshall and J. Hodgson in Nature Biotechnology, volume 16, January 1998, p. 27–31
(9) WO-A-98 01533
(10) U.S. Pat. No. 5,721,435
(11) WO-98/28623
(12) WO-98/38490
(13) EP-A-0 640 826

What is claimed is:

1. A device for reading a biochip comprising plural molecular recognition areas and plural optical positioning marks, in real time, the plural molecular recognition areas comprising fragments of DNA or RNA and occupying predetermined positions relative to the optical positioning marks, the device comprising:
   an optical head configured to project incident light onto the biochip,
   means for relatively displacing the head relative to the biochip, configured to scan over the biochip,
   an optical analysis system comprising,
      a first optical system associated with said optical head to project light possibly coming from recognition areas, onto at least a first electro-optic sensor, and
      a second optical system associated with the optical head to project any light from at least one positioning mark, onto at least one second electro-optic sensor, and
   means for servocontrolling the means for relatively displacing as a function of electrical signals from the electro-optic sensor in the optical analysis system,
   wherein the means for relatively displacing comprise means for macroscopic displacement and means for microscopic displacement, and
   wherein the means for servocontrolling is connected to the means for microscopic displacement.

2. The device according to claim 1, wherein the optical analysis system is a confocal optical system.

3. The device according to claim 1, wherein the first electro-optic sensor, receiving light emitted by target molecules present on the plural molecular recognition areas, is sensitive to at least one of fluorescent light, reflection light, and hybridization detection light by variation of mass, and at least one of thickness and index and light representative of photo-thermal effects.

4. The device according to claim 1, wherein the first electro-optic sensor is optically connected to the first optical system through an optical fiber.

5. The device according to claim 1, wherein the first and second optical systems are coupled to the optical head through a dichroic slide.

6. The device according to claim 1, wherein the optical head comprises a focusing lens and at least one of an axial displacement actuator and a lateral displacement actuator for focusing the lens, and further comprising a third optical system associated with the optical head to project light produced by reflection of incident light on the biochip onto a third electro-optic sensor, and focusing means for servocontrolling connected to the actuator to control the lens focusing displacement.

7. The device according to claim 1, further comprising at least one electro-optic sensor common to the first and second optical systems, said common electro-optic sensor collecting light originating from the plural molecular recognition areas and light originating from at least one positioning mark, and connected to the means for servocontrolling scanning by the optical head.

8. A biochip comprising plural molecular recognition areas and plural optical positioning marks, wherein the plural molecular recognition areas are at least partly superposed on optical positioning marks so as to cover at least some of said optical positioning marks.

9. The biochip according to claim 8, wherein the optical positioning marks are almost transparent to at least one fluorescent light that could be emitted from the plural molecular recognition areas in response to at least one incident reading light.

10. The biochip according to claim 8, wherein the plural molecular recognition areas are in predetermined locations relative to the optical positioning marks.

11. The biochip according to claim 8, wherein one of said optical positioning marks is associated with each molecular recognition area.

12. The biochip according to claim 8, wherein the plural molecular recognition areas are arranged in rows and in columns, and at least one of said optical positioning marks is associated with at least one of a row and a column in the plural molecular recognition areas.

13. The biochip according to claim 8, wherein the optical positioning marks comprise strips configured to reflect incident light, the percentage of reflected light being less than 50%.

14. The biochip according to claim 8, wherein the optical positioning marks comprise strips with a textured surface configured to introduce a phase shift in incident light.

15. The biochip according to claim 8, wherein the optical positioning marks comprise positioning tracks made of at least one of a diffusing material and a fluorescent material extending along rows of the plural molecular recognition areas, and reflecting strips laid out on the said positioning tracks.

16. The biochip according to claim 8, wherein the optical positioning marks comprise reflecting tracks with a coefficient of reflection of less than 50%, extending along rows of the plural molecular recognition areas, the tracks including local non-reflecting areas.

17. The biochip according to claim 8, wherein adjacent regions of optical positioning marks are provided with a different optical path for incident light.

18. The biochip according to claim 8, wherein adjacent optical positioning marks are made from materials with reflectivities of less than 50%, and are different from each other.

19. The biochip according to claim 18, wherein adjacent regions of optical positioning marks have different physical thicknesses.

20. The biochip according to claim 8, wherein adjacent regions of optical positioning marks have different dopings.

21. The biochip according to claim 8, comprising an intermediate layer between the optical positioning marks and a coating on the molecular recognition areas, wherein the index and the reflectivity of the said intermediate layer are configured to form a dichroic mirror.

22. The biochip according to claim 8, wherein the reflectivity of the optical positioning marks an interface between the plural molecular recognition areas and the optical positioning marks is between 1% and 10% for a light beam reaching the biochip through a face called a back face, opposite the face on which recognition molecules are located.

23. The biochip according to claim 8, wherein the reflectivity of the optical positioning marks and/or an interface between a coating material on the plural molecular recognition areas and the optical positioning marks is between 1% and 100% for a light beam arriving at a face of the biochip coated with the coating material.

24. The biochip according to claim 8, wherein the optical positioning marks comprise regions of bi-refringent material configured to modify a polarization direction of polarized incident light.

25. The biochip according to claim 8, wherein the plural molecular recognition areas have a transparent bond layer.

26. The biochip according to claim 8, wherein the plural molecular recognition areas are coated with reagents chosen among chemical or biological reagents comprising at least one of DNA probes, antibodies, and antigens.

27. A process for reading a biochip comprising several molecular recognition areas and several optical positioning marks associated with plural molecular recognition areas, comprising the steps of:

using a device for reading a biochip comprising plural molecular recognition areas and plural optical positioning marks, in real time, the plural molecular recognition areas comprising fragments of DNA or RNA and occupying predetermined positions relative to the optical positioning marks, the device comprising,
an optical head configured to project incident light onto the biochip,
means for relatively displacing the head relative to the biochip, configured to scan over the biochip,
an optical analysis system comprising,
a first optical system associated with said optical head to project light possibly
coming from recognition areas, onto at least a first electro-optic sensor, and
a second optical system associated with the optical head to project any light from at least one positioning mark, onto at least one second electro-optic sensor, and
means for servocontrolling the means for relatively displacing as a function of electrical signals from the electro-optic sensor in the optical analysis system,
wherein the means for relatively displacing comprises means for macroscopic displacement and means for microscopic displacement, and
wherein the means for servocontrolling is connected to the means for microscopic displacement;
continuously acquiring read signals originating from a sensor in the optical analysis system by scanning across a sequence of recognition areas; and
normalizing said acquired signals as a function of the time elapsed between when the optical head passes over successive positioning marks associated with said scanned recognition areas.

28. A process for reading a biochip comprising plural molecular recognition areas and plural optical positioning marks associated with plural molecular recognition areas, comprising the steps of:

using a device for reading a biochip comprising plural molecular recognition areas and plural optical positioning marks, in real time, the plural molecular recognition areas comprising fragments of DNA or RNA and occupying predetermined positions relative to the optical positioning marks, the device comprising,
an optical head configured to project incident light onto the biochip,
means for relatively displacing the head relative to the biochip, configured to scan over the biochip,
an optical analysis system comprising,
a first optical system associated with said optical head to project light possibly
coming from recognition areas, onto at least a first electro-optic sensor, and
a second optical system associated with the optical head to project any light
from at least one positioning mark, onto at least one second electro-optic sensor, and
means for servocontrolling control the means for relatively displacing as a function of electrical signals from the electro-optic sensor in the optical analysis system, wherein the means for relatively displacing comprise means for macroscopic displacement and means for microscopic displacement, and wherein the means for servocontrolling is connected to the means for microscopic displacement;

continuously acquiring read signals originating from a sensor in the optical analysis system by scanning across a sequence of recognition areas; and continuously servocontrolling a relative displacement speed between the optical head and the biochip to the time measured between successive passes of the optical head over successive positioning marks associated with the said scanned recognition areas.

29. The biochip according to claim 8, wherein the optical positioning marks comprise strips configured to slightly reflect incident light, the percentage of reflected light being less than approximately 5%.

30. The biochip according to claim 8, wherein the optical positioning marks comprise slightly reflecting tracks with a coefficient of reflection of less than approximately 5%, extending along rows of the plural molecular recognition areas, the tracks including local non-reflecting areas.

31. The biochip according to claim 8, wherein adjacent optical positioning marks are made from materials with low reflectivities of less than approximately 5%, and are different from each other.

\* \* \* \* \*